United States Patent
Nesvadba et al.

(10) Patent No.: US 6,503,937 B1
(45) Date of Patent: Jan. 7, 2003

(54) OXOBENZOFURANYLIDE-DIHYDROINDOLONE

(75) Inventors: Peter Nesvadba, Marly (CH); Joachim Jandke, Steinen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/806,741

(22) PCT Filed: Oct. 11, 1999

(86) PCT No.: PCT/EP99/07593

§ 371 (c)(1),
(2), (4) Date: Apr. 3, 2001

(87) PCT Pub. No.: WO00/24736

PCT Pub. Date: May 4, 2000

(30) Foreign Application Priority Data

Oct. 22, 1998 (CH) .............................................. 2138/98

(51) Int. Cl.$^7$ ..................... A61K 31/404; C07D 405/04
(52) U.S. Cl. ........................................ 514/414; 548/463
(58) Field of Search ........................... 548/463; 514/414

(56) References Cited

U.S. PATENT DOCUMENTS 3,305,560 A  *  2/1967 Plostnicks

FOREIGN PATENT DOCUMENTS

WO            99/13007         3/1999

OTHER PUBLICATIONS

C. Marschalk, Bulletin De La Societe Francaise De France, FR, Societe Francaise de Chimie, vol. 9, No. 5, (1942), pp. 826–832.
D.N. Nicolaides et al., Journal of the Chemical Society, Perkin Transactions 1, GB, Chemical Society, Letchworth 1, (1992), pp. 2479–2484.
M. Marschalk, Bulletin De La Societe Chimique de France, (1942), pp. 801–804.
R. Stolléet al., Berichte der Deutschen Chemischen Gesellschaft, vol. 54, (1921), pp. 1213–1220.

* cited by examiner

Primary Examiner—Ceila Chang
Assistant Examiner—Sonya Wright
(74) Attorney, Agent, or Firm—David R. Crichton

(57) ABSTRACT

Oxobenzofuranylidene-dihydroindolones of formulae trans-(Ia) and cis-(Ib)

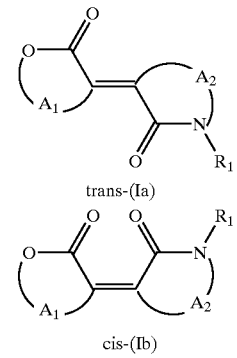

and of formulae trans-(IIa) and cis-(IIb)

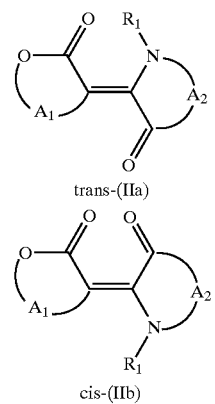

wherein
$A_1$ and $A_2$ are each independently of the other unsubstituted or mono- to tetra-substituted ortho-$C_6$–$C_{18}$arylene, and $R_1$ is hydrogen or an organic radical, with the proviso that when $R_1$ is hydrogen and $A_2$ is 1,2-phenylene, $A_1$ is not 9,10-anthraquinon-1,2-ylene, 4-chloro-3,5-dimethyl-1,2-phenylene or 3,5-dimethyl-1,2-phenylene, processes for their preparation and the use thereof.

5 Claims, No Drawings

OXOBENZOFURANYLIDE-DIHYDROINDOLONE

This application is a 371 of PCT/E99/07593 filed Oct. 11, 1999.

The present invention relates to oxobenzofuranylidene-dihydroindolones, to processes for their preparation and to the use thereof.

Bull. Soc. Chim. Fr., (1942), pages 801–804, describes a trans-3-(2-oxo-benzofuran-3-ylidene)-1,3-dihydro-indol-2-one (the reaction product of phthaloyl-6,7-coumarone-2 and isatin) and a trans-2-(2-oxo-benzofuran-3-ylidene)-1,2-dihydro-indol-3-one (the reaction product of phthaloyl-6,7-coumarone-2 and α-isatinanilide).

Chem. Ber., Volume 54, (1921), pages 1213–1220, describes two 2-(2-oxo-benzofuran-3-ylidene)-1,2-dihydro-indol-3-ones: on the one hand, the condensation product of 4,6-dimethyl-coumarandione with indoxyl, and the condensation product of 5-chloro-4,6-dimethyl-coumarandione with indoxyl.

It is a disadvantage of the known processes that preparation is too complicated and too expensive for large-scale and commercial purposes.

The invention was therefore based on the problem of providing further oxobenzofuran-ylidene-dihydroindolones, which should preferably be suitable as colourants or fluorescent agents, especially for colouring or pigmenting organic or inorganic, high or low molecular weight material, especially high molecular weight organic material. The problem was also to find an economic process for the preparation of oxobenzofuranylidene-dihydroindolones. There have accordingly been found oxobenzofuranylidene-dihydroindolones of formulae trans-(Ia) and cis-(Ib)

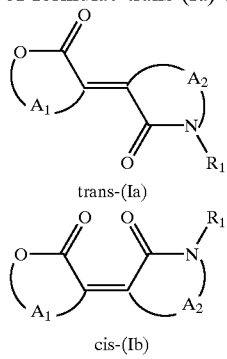

and of formulae trans-(IIa) and cis-(IIb)

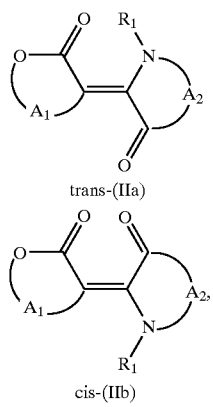

wherein $A_1$ and $A_2$ are each independently of the other unsubstituted or mono- to tetra-substituted ortho-$C_6$–$C_8$arylene, and $R_1$ is hydrogen, $C_1$–$C_{25}$alkyl, $C_5$–$C_{12}$cycloalkyl, $C_6$–$C_{24}$aryl, a heteroaromatic radical, —$(CH_2)_n$—$COR_2$ or —$(CH_2)_m$—$OR_3$, wherein $R_2$ is hydroxy, —OX, or, unsubstituted or mono- or poly-substituted by hydroxy, —OX or by amino, $C_1$–$C_{25}$alkoxy, $C_1$–$C_{25}$alkylamino or $C_1$–$C_{25}$dialkyl-amino, di($C_6$–$C_{24}$aryl)amino, $C_1$–$C_{12}$alkyl, $C_2$–$C_{24}$alkenyl, and X is a cation, and $R_3$ is hydrogen or —CO—($C_1$–$C_{25}$alkyl), and n and m denote each independently of the other a whole number in the range from 0 to 6, and a single C—C bond also may have been replaced by a corresponding ether unit, C—O—C, with the proviso that, when $R_1$ is hydrogen and $A_2$ is 1,2-phenylene, $A_1$ is not 9,10-anthraquinon-1,2-ylene, 4-chloro-3,5-dimethyl-1,2-phenylene or 3,5-dimethyl-1,2-phenylene.

Furthermore, improved processes for the preparation of oxobenzofuranylidene-dihydro-indolones and the use thereof have been found.

According to the invention X is a cation of an alkali metal such as lithium, sodium, potassium, an alkaline earth metal such as magnesium, calcium, strontium or is copper, zinc or aluminium or a quaternary amine such as $[NR_4R_5R_6R_7]^+$, wherein $R_4$ and $R_5$ are each independently of the other hydrogen, $C_1$–$C_{25}$alkyl, $C_6$–$C_{18}$aryl or $C_7$–$C_{28}$aralkyl, and $R_6$ and R7 are each independently of the other hydrogen, $C_6$–$C_{18}$aryl, $C_7$–$C_{18}$aralkyl or, unsubstituted or mono- or poly-substituted by halogen, hydroxy or by $C_1$–$C_{12}$alkoxy, $C_1$–$C_{25}$alkyl or $C_2$–$C_{24}$alkenyl, or $R_6$ and $R_7$ together with the common nitrogen atom denote an unsubstituted or mono- to tetra-$C_1$–$C_4$alkyl-substituted pyrrolidine, piperidine, piperazine or morpholine, carbazole, phenoxazine or phenothiazine radical.

In a preferred embodiment, $A_1$ and $A_2$ are each independently of the other ortho-$C_6$–$C_{18}$-arylene, which may be, for example, substituted or unsubstituted 1,2-phenylene, 1,2-naphthylene, 2,3-naphthylene, 1,2-phenanthrylene, 2,3-phenanthrylene, 3,4-phenanthrylene, 9,10-phenanthrylene, 1,2-anthracenyl, 2,3-anthracenyl or 1,2-anthraquinonylene, 2,3-anthraquinonylene.

Substituents that come into consideration for ortho-$C_6$–$C_{18}$arylene are, for example, bivalent radicals such as 1,3-butadien-1,4-ylene or —CH=CH—NH—, or fused-on substituted or unsubstituted 5- or 6-membered rings, and also, if desired, other substituents (see below).

In an especially preferred embodiment, $A_1$ is

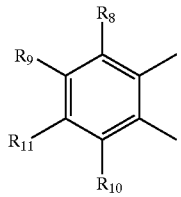

and $A_2$ is

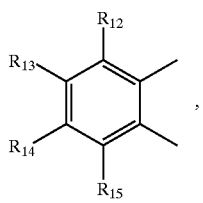

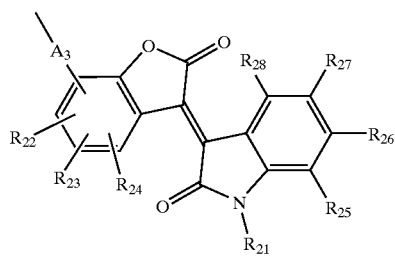

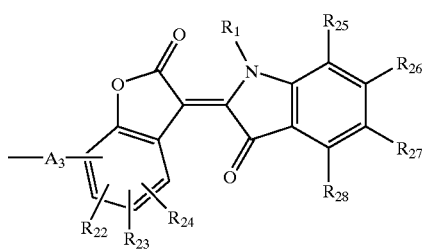

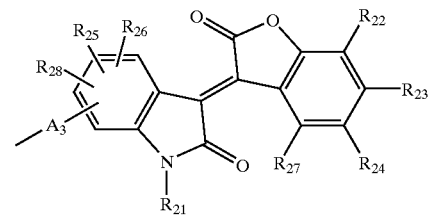

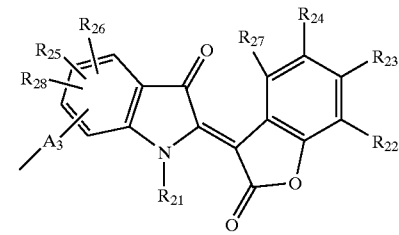

$R_8$, $R_9$, $R_{11}$, $R_{10}$, $R_{12}$, $R_{13}$, $R_{14}$ and $R_{15}$ being each independently of the others hydrogen, halogen, cyano, —$NO_2$, —$R_{16}$, —$NR_{17}R_{18}$, —$NR_{19}COR_{17}$, —$NR_{19}COOR_{17}$, —$N=CR_{17}R_{18}$, —$CONR_{19}R_{20}$, —$OR_{17}$, —O—($C_1$-$C_{12}$alkylene)-COOX, —O—($C_1$-$C_{12}$alkylene) -COOH, —O—($C_1$-$C_{12}$alkylene)—O—CO—$R_{17}$, —O—($C_1$-$C_{12}$alkylene)-$COOR_{17}$, —O—($C_1$-$C_{12}$alkylene)-$CONR_{19}R_{20}$, —O—($C_1$-$C_{12}$alkylene)-$OR_{17}$, —($C_1$-$C_{12}$alkylene)-O—CO—$R_{17}$, —($C_1$-$C_{12}$alkylene)-$OR_{17}$, —$COOR_{17}$, —($C_1$-$C_{12}$alkylene)-$COOR_{17}$, —($C_1$-$C_{12}$alkylene)-$CONR_{19}R_{20}$, —($C_1$-$C_{12}$alkylene)-COOX, —($C_1$-$C_{12}$alkylene)-COOH, —COOX, —COOH, —$SR_{17}$, —$SOR_{17}$, —$SO_2R_{17}$, —$SO_2NR_{19}R_{20}$, —$SO_3R_{17}$, $SO_3H$ or $SO_3X$, wherein $R_{17}$, $R_{18}$, $R_{19}$ and $R_{20}$ are each independently of the others hydrogen or $R_{16}$, and $R_{16}$ is, unsubstituted or mono- or poly-substituted by halogen, hydroxy, amino, oxo, carboxy, cyano, —$COOR_{18}$- or by —COOX, $C_1$-$C_{25}$alkyl, $C_5$-$C_{12}$cycloalkyl or $C_2$-$C_{24}$alkenyl, which may be uninterrupted or interrupted one or more times by O, S or N—($C_1$-$C_{25}$alkyl), N—($C_2$-$C_{24}$alkenyl) when the alkyl has more than two and the alkenyl more than three carbon atoms, or is, unsubstituted or mono- or poly-substituted by halogen, nitro, cyano, —$OR_{18}$, —$S_{18}$, —$NR_{19}R_{20}$, —$CONR_{19}R_{20}$, —$COOR_{18}$, —COOX, —COOH, —$SO_2R_{18}$, —$SO_2NR_{19}R_{20}$, —$SO_3R_{18}$, —$SO_3X$, —$SO_3H$, —$NR_{19}COR_{18}$ or by —$NR_{19}COOR_{18}$, $C_6$-$C_{18}$aryl, $C_7$-$C_{18}$aralkyl or heteroaryl, or $R_{19}$ and $R_{20}$, together with the nitrogen atom linking them, are unsubstituted or mono- to tetra-$C_1$-$C_4$alkyl-substituted pyrrolidinyl, piperidyl, piperazinyl or morpholinyl, or are carbazolyl, phenoxazinyl or phenothiazinyl, it being possible, optionally, for $R_8$ and $R_9$, $R_9$ and $R_{11}$, $R_{11}$ and $R_{10}$ and for $R_{12}$ and $R_{13}$, $R_{13}$ and $R_{14}$ or $R_{14}$ and $R_{15}$ additionally to form, in each case, a substituted or unsubstituted 5- or 6-membered ring.

In a further especially preferred embodiment, at least one of the substituents $R_8$, $R_9$, $R_{11}$, $R_{10}$, $R_{12}$, $R_{13}$, $R_{14}$ and $R_{15}$ is a radical selected from the group consisting of the radicals $Z_1$, $Z_2$, $Z_3$ and Z4 wherein $R_{22}$, $R_{23}$, $R_{24}$, $R_{25}$, $R_{26}$, $R_{27}$ and $R_{28}$ are each independently of the others hydrogen, halogen, cyano, —$NO_2$, —$R_{16}$, —$NR_{17}R_{18}$, —$NR_{19}COR_{17}$, —$NR_{19}COOR_{17}$, —$N=CR_{17}R_{18}$, —$CONR_{19}R_{20}$, —$OR_{17}$, —O—($C_1$-$C_{12}$alkylene)-COOX, —O—($C_1$-$C_{12}$alkylene)-COOH, —O—($C_1$-$C_{12}$alkylene)-O—CO—$R_{17}$, —O—($C_1$-$C_{12}$alkylene)-$COOR_{17}$, —O—($C_1$-$C_{12}$alkylene)-$CONR_{19}R_{20}$, —O—($C_1$-$C_{12}$alkylene)-$OR_{17}$, —($C_1$-$C_{12}$alkylene)-O—CO—$R_{17}$, —($C_1$-$C_{12}$alkylene)-$OR_{17}$, —$COOR_{17}$, —($C_1$-$C_{12}$alkylene)-$COOR_{17}$, —($C_1$-$C_{12}$alkylene)-$CONR_{19}R_{20}$, —($C_1$-$C_{12}$alkylene)-COOX, —COOX, —COOH, —$SR_{17}$, —$SOR_{17}$, —$SO_2R_{17}$, —$SO_2NR_{19}R_{20}$, —$SO_3R_{17}$ or $SO_3X$, $SO_3H$, the radicals $R_{17}$, $R_{18}$, $R_{19}$, $R_{20}$ being as defined above, and $R_{21}$, independently of $R_1$, has the same definition as $R_1$, and $A_3$ is a single bond or is, unsubstituted or mono- or poly-substituted by $C_1$-$C_{25}$alkyl, $C_6$-$C_{24}$aryl, halogen, hydroxy, —OX, oxo, cyano, —$COOR_6$, —COOX, —COOH, —$SO_3R_6$, —$SO_3X$ or by —$SO_3H$, $C_1$-$C_{24}$alkylene or $C_5$-$C_{12}$cycloalkylene or —OOC—($C_1$-$C_{24}$alkylene)-COO—, —COO—($C_1$-$C_{24}$alkylene)-OOC—, —$NR_{19}CO$—($C_1$-$C_{24}$alkylene)-$CONR_{19}$—, —$CONR_{19}$—($C_1$–$C_{24}$alkylene)—$NR_{19}CO$—;
$C_6$–$C_{24}$arylene or heteroarylene.

A further especially preferred embodiment relates to oxobenzofuranylidene-dihydroindolones wherein $A_1$ is

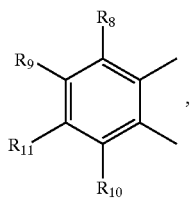, wherein $R_8$, $R_9$, $R_{11}$ and $R_{10}$ are as defined above, and $A_2$ is a bivalent radical $Z_5$ or $Z_6$

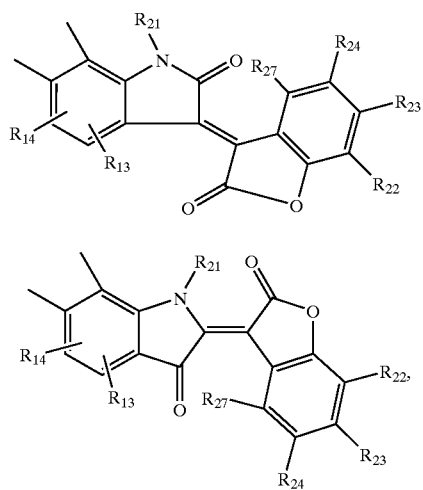

wherein $R_{13}$, $R_{14}$, $R_{21}$, $R_{22}$, $R_{23}$, $R_{24}$ and $R_{27}$ are as defined above.

A further preferred embodiment relates to oxobenzofuranylidene-dihydroindolone of formula (LI)

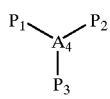 (LI)

wherein
  $P_1$, $P_2$, $P_3$ are each independently of the others a radical selected from the group consisting of the radicals $Z_1$, $Z_2$, $Z_3$ and $Z_4$, and $A_4$ is a trivalent radical, preferably

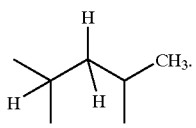

The compounds according to the invention may occur in various crystalline modifications.

Alkyl, alkenyl or alkylene may be straight-chained, branched, monocyclic or polycyclic. Preference is given to $C_1$–$C_{25}$alkyl, $C_2$–$C_{24}$alkenyl or $C_1$–$C_{24}$alkylene.

$C_1$–$C_{25}$Alkyl is therefore, for example, very especially, $C_1$–$C_4$alkyl, e.g. methyl, ethyl, n-propyl, isopropyl, n-butyl, sec-butyl, isobutyl, tert-butyl, more especially $C_1$–$C_6$alkyl, which is as defined for $C_1$–$C_4$alkyl and is additionally n-pentyl, 2-pentyl, 3-pentyl, 2,2-dimethylpropyl, n-hexyl, and especially $C_1$–$C_8$alkyl, which is as defined for $C_1$–$C_6$alkyl and is additionally, for example, n-octyl, 1,1,3,3-tetramethylbutyl and 2-ethylhexyl, and preferably $C_1$–$C_{12}$alkyl, which is as defined for $C_1$–$C_8$alkyl and is additionally decyl or dodecyl, and also $C_1$–$C_{25}$alkyl, which is as defined for $C_1$–$C_{12}$alkyl and may additionally be tetradecyl, pentadecyl, hexadecyl, heptadecyl, octadecyl, icosyl, henicosyl, docosyl, tetracosyl or pentacosyl.

Examples of mono- or poly-cyclic alkyl radicals that may be mentioned include: $C_4$–$C_{12}$cycloalkyl such as cyclobutyl, cyclopentyl, cyclohexyl, cycloheptyl, cyclooctyl, cyclononyl, cyclodecyl, cycloundecyl or cyclododecyl, trimethylcyclohexyl, menthyl, thujyl, bornyl, 1-adamantyl and 2-adamantyl, especially $C_5$–$C_{12}$cycloalkyl such as cyclopentyl, cyclohexyl, cycloheptyl, cyclooctyl, cyclononyl, cyclodecyl, cycloundecyl or cyclododecyl.

$C_1$–$C_{24}$Alkylene is, for example, methylene, ethylene, n-propylene, isopropylene, n-butylene, sec-butylene, isobutylene, tert-butylene, n-pentylene, 2-pentylene, 3-pentylene, 2,2-dimethylpropylene, n-hexylene, n-octylene, 1,1,3,3-tetramethylbutylene, 2-ethylhexylene, nonylene, decylene, menthylene, dodecylene, tetradecylene, hexadecylene, heptadecylene, octadecylene, icosylene, henicosylene, docosylene or tetracosylene, preferably $C_1$–$C_{12}$alkylene such as methylene, ethylene, n-propylene, isopropylene, n-butylene, sec-butylene, isobutylene, tert-butylene, n-pentylene, 2-pentylene, 3-pentylene, 2,2-dimethylpropylene, n-hexylene, n-octylene, 1,1,3,3-tetramethylbutylene, 2-ethylhexylene, nonylene, decylene, especially $C_1$–$C_8$alkylene such as methylene, ethylene, n-propylene, isopropylene, n-butylene, sec-butylene, isobutylene, tert-butylene, n-pentylene, 2-pentylene, 3-pentylene, 2,2-dimethylpropylene, n-hexylene, n-octylene, 1,1,3,3-tetramethylbutylene, 2-ethylhexylene, more especially $C_1$–$C_6$alkylene such as methylene, ethylene, n-propylene, isopropylene, n-butylene, sec-butylene, isobutylene, tert-butylene, n-pentylene, 2-pentylene, 3-pentylene, 2,2-dimethylpropylene, n-hexylene and very especially $C_1$–$C_4$alkylene such as methylene, ethylene, n-propylene, isopropylene, n-butylene, sec-butylene, isobutylene, tert-butylene.

Examples of mono- or poly-cyclic alkylene radicals that may be mentioned include: $C_4$–$C_{12}$cycloalkylene such as cyclobutylene, cyclopentylene, cyclohexylene, cycloheptylene, cyclooctylene, cyclononylene, cyclodecylene, cycloundecylene and cyclododecylene, trimethylcyclohexylene, thujylene, bornylene, 1-adamantylene and 2-adamantylene.

$C_2$–$C_{24}$Alkenyl is, for example, vinyl, allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2,5-hexadien-2-yl, or the various isomers of hexenyl, octenyl, nonenyl, decenyl, dodecenyl, tetradecenyl, hexadecenyl, heptadecenyl, octadecenyl, icosenyl, henicosenyl, docosenyl or tetracosenyl, being especially $C_2$–$C_{12}$-alkenyl such as vinyl, allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2,5-hexadien-2-yl, or the various isomers of hexenyl, octenyl, nonenyl, decenyl, dodecenyl.

Examples of mono- or poly-cyclic alkenyl radicals that may be mentioned include: $C_4$–$C_{12}$cycloalkenyl such as 2-cyclobuten-1-yl, 2-cyclopenten-1-yl, 2-cyclohexen-1-yl, 2-cyclohexen-1-yl, 3-cyclohexen-1-yl, 2,4-cyclohexadien-1-yl and also 1-p-menthen-8-yl, 4(10)-thujen-10-yl 2-norbornen-1-yl, 2,5-norbornadien-1-yl, 7,7-dimethyl-2,4-norcaradien-3-yl.

$C_1-C_{25}$Alkoxy is $-O-C_1-C_{25}$alkyl, preferably $-O-C_1-C_{12}$alkyl and especially $-O-C_1-C_4$alkyl, the alkyl radicals being as defined above.

$C_1-C_{25}$alkylamino is $-NH-C_1-C_{25}$alkyl, preferably $-NH-C_1-C_{12}$alkyl and especially $-NH-C_1-C_4$alkyl, the alkyl radicals being as defined above.

$C_1-C_{25}$Dialkylamino is $-N-(C_1-C_{25}$alkyl$)_2$, preferably $-N-(C_1-C_{12}$alkyl$)_2$ and especially $-N-(C_1-C_4$alkyl$)_2$, the alkyl radicals being as defined above.

Di($C_6-C_{24}$aryl)amino is ($C_6-C_{24}$aryl$)_2$N— or ($C_6-C_{12}$aryl$)_2$N—, preferably ($C_6-C_{12}$aryl$)_2$N—.

$C_6-C_{24}$Aryl is, for example, phenyl, 1-naphthyl, 2-naphthyl, 4-biphenyl, phenanthryl, 2- or 9-fluorenyl or anthracenyl, preferably $C_6-C_{12}$aryl such as phenyl, 1-naphthyl, 2-naphthyl, 4-biphenyl.

A single C—C bond may also have been replaced by a corresponding ether unit such as C—O—C; for example, there may be obtained $-CH_2-CH_2-O-CH_2-CH_3$ in the case of $C_4$alkyl or $-CH_2-CH_2-O-CH_2-CH_2-O-CH_2-CH_3$ in the case of $C_6$alkyl.

Oxo-substituted $C_1-C_{12}$alkyl means that at least one methylene group has been replaced by a carbonyl group, for example $-C(=O)-CH_3$ in the case of $C_2$alkyl.

Alkyl may be both provided with an oxo unit and interrupted by an —O— unit (provided, of course, that at least two carbon atoms are present in the chain), for example $-(CH_2)_3-O-C(=O)-C(CH_3)_3$, $-C(=O)-(CH_2)_6-OCH_3$ or $-C(CH_3)_2-COO-(CH_2)_3-CH_3$, $-C(=O)-(CH_2)_6-OCH_2-$ or $-C(CH_3)_2-COO-(CH_2)_3-CH_2-$, or preferably, for example, $-O-(C_1-C_6$alkylene$)-COO(C_1-C_6$alkyl$)$ such as $-O-CH_2-COOCH_3$, $-O-(CH_2)_2-COOCH_3$, $-O-(CH_2)_3-COOCH_3$ or $-O-(C_1-C_6$alkylene$)-COOH$ such as $-O-CH_2-COOH$ or $-O-(CH_2)_2-COOH$.

$C_7-C_{28}$Aralkyl is, for example, benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-icosyl or ω-phenyl-docosyl, preferably $C_7-C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and especially $C_7-C_{12}$aralkyl such as benzyl, 2-benzyl-2-propyl, β-phenyl-ethyl, α,α-dimethylbenzyl, ω-phenyl-butyl, ω,ω-dimethyl-ω-phenyl-butyl or ω-phenyl-dodecyl.

As heteroaryl there may be used a polyunsaturated heterocyclic radical having from 5 to 18 atoms selected from the group consisting of C, N, O and S and containing at least 6 conjugated π-electrons, for example thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythiinyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, preferably the mono- or bi-cyclic heteroaromatic radicals mentioned above.

Halogen or Hal is chlorine, bromine, fluorine or iodine, preferably fluorine or chlorine. $C_1-C_{12}$Alkyl or $C_2-C_{12}$alkenyl mono- or poly-substituted by halogen, hydroxy, $C_1-C_{12}$alkoxy or by cyano is, for example, 2-chloro-ethyl, trifluoromethyl, pentafluoroethyl, β,β,β-trifluoroethyl, trichlorovinyl, ω-chloro-propyl, ω-bromo-butyl, perfluorohexyl, perfluorododecyl, 2-hydroxy-ethyl, 2-methoxy-ethyl, 2-ethoxy-ethyl, 2-butoxy-ethyl, 2,3-dihydroxy-propyl, 2,3-dimethoxy-propyl 2,3dimethoxy-propyl or 2-cyano-ethyl, preferably trifluoromethyl, 2-hydroxy-ethyl, 2-methoxy-ethyl, 2-ethoxy-ethyl or 2-cyano-ethyl.

Especially preferred oxobenzofuranylidene-dihydroindolones are compounds of formulae

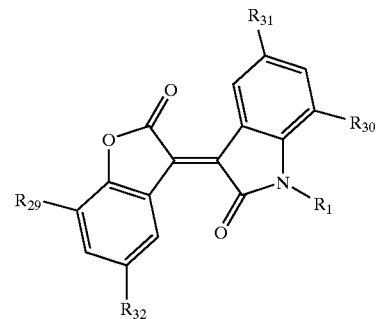

trans-(XXIII)

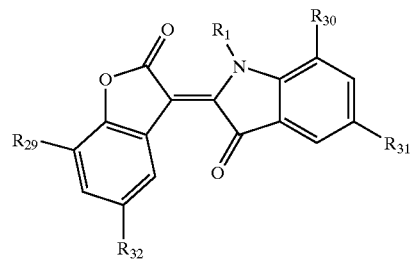

trans-(XXIV)

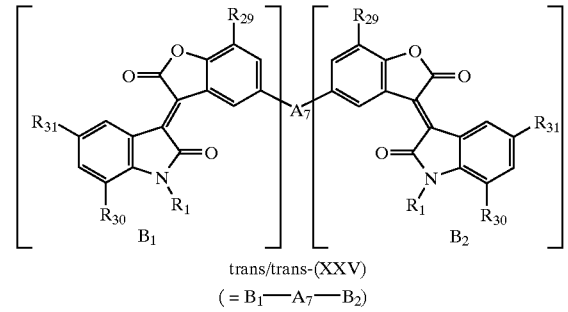

trans/trans-(XXV)

( = $B_1$—$A_7$—$B_2$)

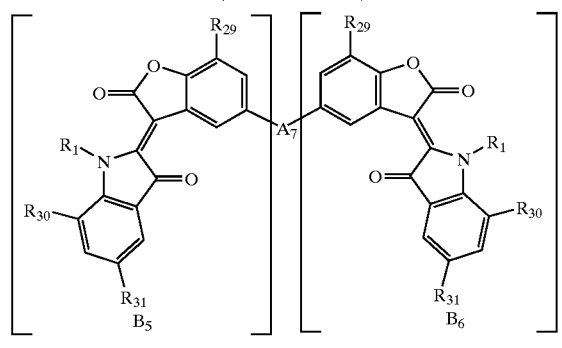

trans/trans-(XXVI)

(= $B_5$—$A_7$—$B_6$)

Wherein
$R_{29}$, $R_{32}$, $R_{30}$ and $R_{31}$ are each independently of the others hydrogen, halogen, $-NO_2$, $R_{33}$, $-OR_{34}$, $-SR_{34}$, especially $OC_9$–$C_{18}$alkyl or —O—($C_1$–$C_{12}$alkylene)-COOX, —O—($C_1$–$C_{12}$alkylene)-COOH, —O—($C_1$–$C_{12}$alkylene)-COOR$_{34}$, —O—($C_1$–$C_{12}$alkylene)-O—CO—R$_{34}$, ($C_1$–$C_{12}$alkylene)-O—CO-R$_{34}$, —O—($C_1$–$C_{12}$alkylene)-OR$_{34}$, —($C_1$–$C_{12}$alkylene)-OR$_{34}$, —COOR34, —($C_1$–$C_{12}$alkylene)-COOR$_{34}$, —($C_1$–$C_{12}$alkylene)-CONR$_{35}$R$_{36}$, —($C_1$–$C_{12}$alkylene)-COOX, —($C_1$–$C_{12}$alkylene)-COOH wherein R$_{33}$ is $C_1$–$C_{25}$alkyl which is unsubstituted or mono- or poly-substituted by oxo, cyano or COOX, or by COOH and which may be uninterrupted or interrupted one or more times by O, or is, unsubstituted or mono- or poly-substituted by halogen, nitro, cyano, —OR$_{35}$, —NR$_{35}$R$_{36}$, —CONR$_{35}$R$_{36}$, —NR$_{37}$COR$_{35}$ or by —NR$_{37}$COOR$_{35}$, $C_6$–$C_{10}$aryl or $C_7$–$C_{10}$aralkyl;

R$_{34}$, R$_{35}$, R$_{36}$ are hydrogen or R$_{33}$, and

A$_7$ is a single bond, $C_1$–$C_{24}$alkylene or $C_5$–$C_{12}$cycloalkylene.

Very special preference is given to compounds of formulae

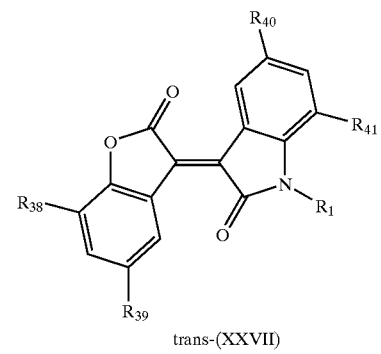

trans-(XXVII)

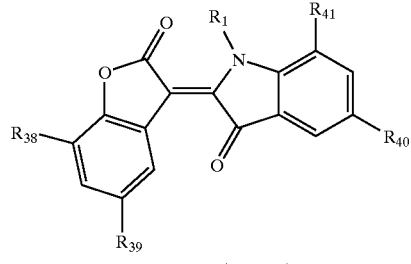

trans-(XXVIII)

wherein

R$_{38}$, R$_{39}$, R$_{41}$ or R$_{40}$ are each independently of the others hydrogen, chlorine or bromine, R$_{42}$ —OR$_{42}$, —SR$_{42}$, especially —OC$_1$–C$_{18}$alkyl or —SC$_1$–C$_{18}$alkyl, wherein R$_{42}$ is $C_1$–$C_{25}$alkyl which is unsubstituted or mono- or poly-substituted by oxo, cyano, —COOH, —COOC$_1$–C$_{18}$alkyl or by —COOX and which may be uninterrupted or interrupted one or more times by O (provided that more than one carbon atom is present), such as especially —O—CH$_2$COOCH$_3$, or is $C_6$–$C_{10}$aryl or $C_7$–$C_{10}$aralkyl.

Very special preference is also given to a compound of formula (XXVII) wherein R$_{38}$ is tert-butyl and R$_{39}$ is —OMe and R$_{41}$ and R$_{40}$ are hydrogen.

In the present invention, cis and trans bisbenzofuranone derivatives of oxobenzofuranylidene-dihydroindolones have also been found, such as

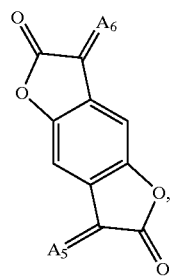 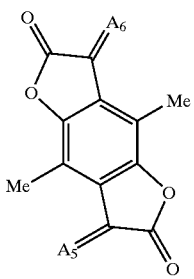

wherein

A$_5$ and A$_6$ denote, in each case independently of the other, two hydrogen atoms, with the proviso that they do not simultaneously denote two hydrogen atoms; they furthermore denote each independently of the other a substituted or unsubstituted isatin radical

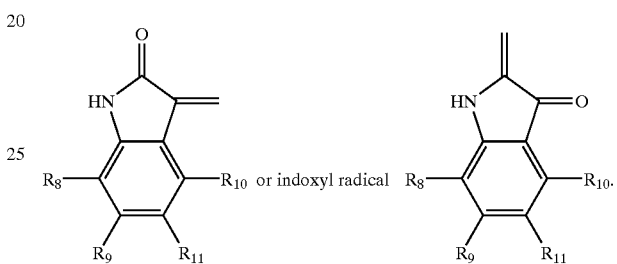

The above bisbenzofuranone derivatives of oxobenzofuranylidene-dihydroindolones are accessible using the processes according to the invention for the preparation of oxobenzofuranylidene-dihydroindolones. They can, for example, be prepared by reacting bisbenzofuranones

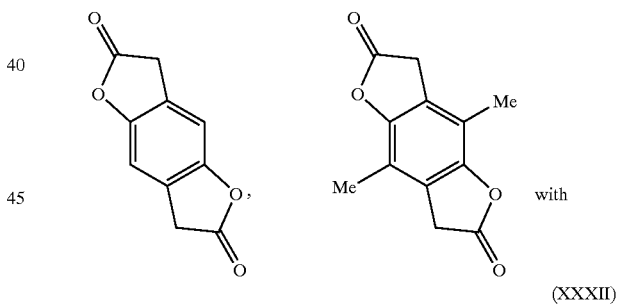

(XXXII)

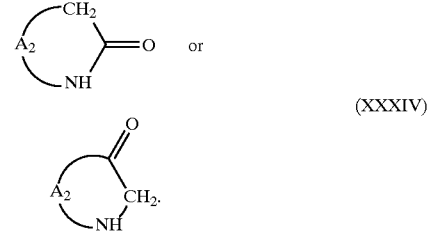

(XXXIV)

The present invention relates also to compositions comprising at least one oxobenzofuranylidene-dihydroindolone according to the invention and, if desired, further oxobenzofuranylidene-dihydroindolones.

An especially preferred embodiment relates to compositions having two oxobenzofuranylidene-dihydroindolones, preferably two compounds selected from the group consisting of the compounds according to the invention and the four compounds from the prior art mentioned at the beginning (trans-3-(2-oxo-benzofuran-3-ylidene)-1,3-dihydro-indol-2-one, trans-2-(2-oxo-benzofuran-3-ylidene)-1,2-dihydro-indol-3-one, the condensation product of 4,6-dimethyl-coumarandione with indoxyl, and the condensation product of 5-chloro-4,6-dimethyl-coumarandione with indoxyl.

The molar ratio of the oxobenzofuranylidene-dihydroindolones in the compositions is usually selected in the range from 99:1 to 1:99.

A further embodiment relates to compositions having three oxobenzofuranylidene-dihydroindolones, preferably having at least one compound according to the invention, the molar ratio usually being selected in the range from 98:1:1 to 1:98:1 or 1:1:98, especially 25:50:25, the totals of the molar ratios always adding up to 100.

The compositions according to the invention can be prepared from the individual compounds by methods of mixing known per se or by means of mixed synthesis (see below).

Mention may be made of the following as especially preferred compounds according to the invention:

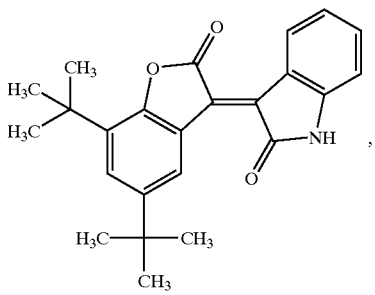

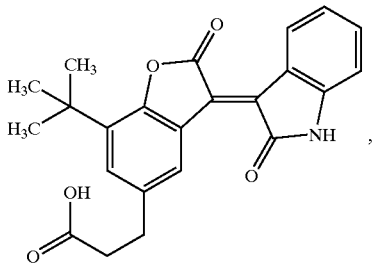

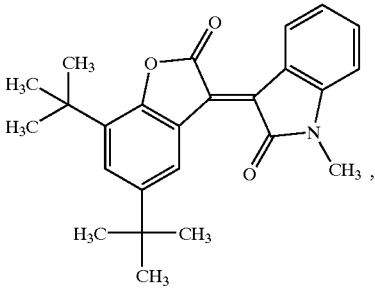

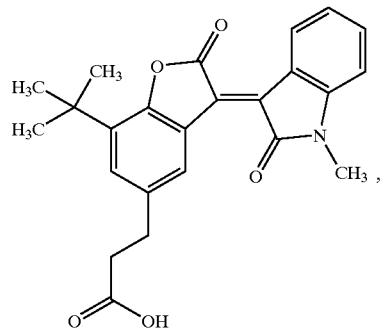

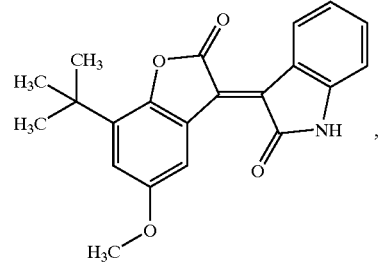

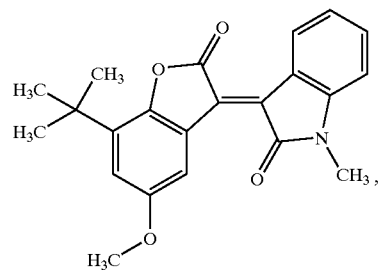

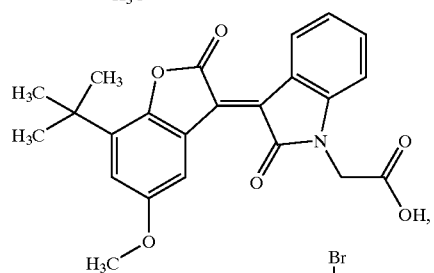

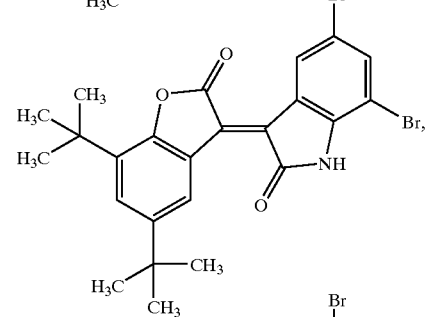

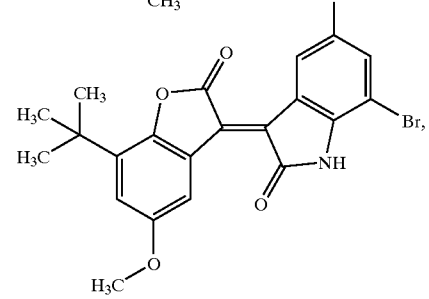

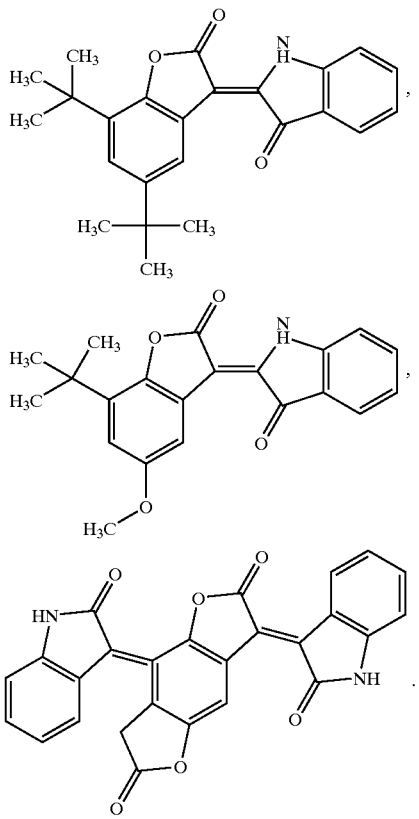

The compounds according to the invention can be prepared analogously to the process described in Bull. Soc. Chim. Fr, (1942), pages 801–804 and 826–832.

The present invention relates also to a process for the preparation of oxobenzofuranylidene-dihydroindolones of formulae trans-(Ia) and cis-(Ib) by reaction of a benzofuranone or bisbenzofuranone derivative with an isatin derivative in the presence of an acidic or basic catalyst, which process comprises reacting a compound of formula (XXIX)

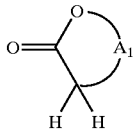 (XXIX)

wherein $A_1$ is as defined above, with a compound of formula (XXX) or (XXXa),

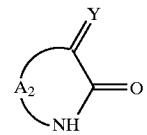 (XXX)

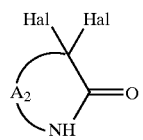 (XXXa)

wherein

Y is O, S, NH, N—($C_1$–$C_{24}$alkyl), N—($C_6$–$C_{18}$aryl) or N—($C_7$–$C_{28}$aralkyl) and Hal is halogen, and $A_2$ is as defined above.

Instead of the carbonyl compounds (XXX) (Y=O) it is, of course, also possible to use corresponding "masked" carbonyl compounds (also referred to hereinbelow as synthetic equivalents) such as Schiff's bases, among others. This also applies to all the processes described hereinbelow.

A further embodiment relates to a process for the preparation of oxobenzofuranylidene-dihydroindolones of formulae trans-(Ia) and cis-(Ib) by reaction of a benzofuranone or bisbenzofuranone derivative with an oxindole derivative in the presence of an acidic or basic catalyst, which process comprises reacting a compound of formula (XXXI) or (XXXIa)

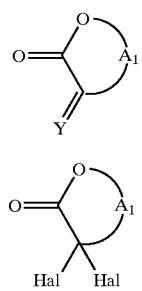 (XXXI)

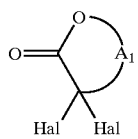 (XXXIa)

with a compound of formula (XXXII)

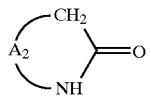 (XXXII)

wherein $A_2$, $A_1$, Y and Hal are as defined hereinabove.

A further embodiment relates to a process for the preparation of compounds of formulae trans-(IIa) and cis-(IIb) by reaction of a benzofuranone or bisbenzofuranone derivative with an indoxyl derivative in the presence of an acid or base, which process comprises reacting a compound of formulae (XXXI) or (XXXIa) with a compound of formula (XXXIV)

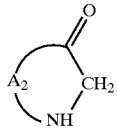 (XXXIV)

wherein $A_2$ is as defined hereinabove.

A further embodiment relates to a process for the preparation of compounds of formulae trans-(Ia), trans-(IIa) or cis-(Ib), cis-(IIb) by reaction of a benzofuranone or bisbenzofuranone derivative with an indoxyl or isatin derivative in the presence of an acid or a base, which process comprises reacting a compound of formula (XXXI) or (XXXIa) with (a) an imine of formula (XXXV)

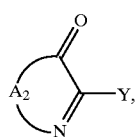

(XXXV)

wherein $A_2$ and Y are as defined hereinabove, or
(b) with a ketal of formulae (XXXVI) or (XXXVII)

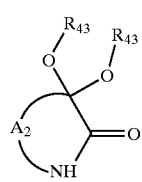

(XXXVI)

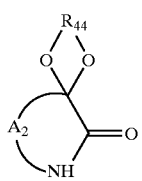

(XXXVII)

wherein
$R_{43}$ is $C_1$–$C_6$alkyl and $R_{44}$ is an unsubstituted or substituted bivalent $C_1$–$C_6$alkylene radical such as, for example, —$CH_2$—$CH_2$—$CH_2$—, —$CH_2$—$C(CH_3)_2$—$CH_2$—, —$CH_2$—$CH_2$—$CH_2$—$CH_2$—, —$CH_2$—$CH_2$—$CH_2$—$CH_2$—, All the processes according to the invention are chemically similar reactions, which correspond to the condensation reactions of so-called C—H acid compounds with an electrophile and are described jointly hereinbelow.

The present invention relates also to mixed syntheses in accordance with processes according to the invention for the preparation of compositions according to the invention, which comprise reacting mixtures of different C—H acid compounds of formulae (XXIX), (XXXIV) or (XXXII) with a carbonyl compound or its synthetic equivalents of formulae (XXX), (XXXa) or (XXXI), (XXXIa)
or
mixtures of different C—H acid compounds of formulae (XXIX), (XXXIV) or (XXXII) with an imine of formula (XXXV) or ketal of formulae (XXXVI), (XXXVII)
or
mixtures of differently substituted carbonyl compounds or their synthetic equivalents of formulae (XXX), (XXXa) or (XXXI), (XXXIa) with a C—H acid component of formulae (XXIX), (XXXIV) or (XXXII)
or
mixtures of different imines of formula (XXXV) or ketals of formulae (XXXVI), (XXXVII) with a C—H acid component of formulae (XXIX), (XXXIV) or (XXXII).

The reactions are usually initiated by adding one reaction component to the other. The order of addition is generally immaterial for the reactions according to the invention.

The molar ratio of the carbonyl compound or its synthetic equivalent of formulae (XXIX), (XXX), (XXXa) or (XXXI), (XXXIa) or an imine of formula (XXXV) or ketal of formula (XXXVII) to the CH acid compound is usually selected in the range from 1.5:1 to 0.5:1, preferably in the range from 1.2:1 to 0.8:1; the ratio is very especially 1:1.

The molar ratio of the bisbenzofuranone to the isatin is generally in the range from 1:5 to 1:1.5 and preferably in the range from 1:3 to 1:2.

It has proved advantageous to carry out the reaction at elevated temperature, especially in the region of the boiling point of the reaction mixture, for example in the range from 20 to 200° C., preferably from 60 to 150° C.

The reaction is usually carried out in the presence of organic solvents. Organic solvents that come into consideration are, for example, alcohols such as ($C_1$–$C_{25}$alkyl)-OH, especially ethanol, methanol, isopropanol or acids such as ($C_1$–$C_{25}$alkyl)-COOH, especially acetic acid, or anhydrides such as ($C_1$–$C_{25}$alkyl)-COOCO—($C_1$–$C_{25}$alkyl) and also dipolar-aprotic solvents such as acetonitrile, benzonitrile, N,N'-dimethylformamide, N,N'-dimethylacetamide, nitrobenzene, N-methylpyrrolidone, aliphatic or aromatic hydrocarbons—which may if desired be halogenated—or mixtures thereof, such as benzine (being a mixture of different, substantially aliphatic hydrocarbons), trichloroethane, benzene or an unsubstituted or alkyl-, alkoxy- or halo-substituted benzene such as toluene, xylene, anisole or chlorobenzene, or esters such as ethyl acetate, butyl acetate or ethers such as, for example, tetrahydrofuran, dioxane, $EtOCH_2CH_2OH$ (e.g. commercially available as Cellosolve® from Fluka) or glycol ethers such as ethylene glycol methyl ether, ethylene glycol ethyl ether, diethylene glycol monomethyl ether or diethylene glycol monoethyl ether, or nitrogen-containing solvents such as pyridine, triethylamine, picoline or quinoline. The above-mentioned solvents can also be used in admixture with one another.

From 1 to 20% by weight of solvent is usually used for one % by weight of the total reactants.

For preparation of compounds of formulae (Ia) or (Ib) it has proved especially advantageous to proceed in an alcoholic or acetic acid solution in the region of the boiling point of the reaction mixture, for example in the range from 100 to 130° C.

Special preference is given to the reaction in the presence of an additional organic or inorganic base or acid, especially in the presence of catalytic amounts of a base or acid. For example, the amount of base or acid is selected in the range from 0.1 to 10 mol %, preferably from 1 to 5 mol %, based on the molar total of the starting materials.

Inorganic bases that come into consideration are, for example, alkali metals such as lithium, sodium or potassium and hydroxides and carbonates thereof such as lithium, sodium or potassium hydroxide or lithium, sodium or potassium carbonate, or alkali metal amides such as lithium, sodium or potassium amide or alkali metal hydrides such as lithium, sodium or potassium hydride or alkaline earth metal or alkali metal alcoholates, of primary, secondary or tertiary aliphatic $C_1$–$C_{10}$alkyl alcohols, such as lithium, sodium or potassium methanolate, ethanolate, n-propanolate, isopropanolate, n-butanolate, sec-butanolate, tert-butanolate, 2-methyl-2-butanolate, 2-methyl-2-pentanolate, isopropanolate, n-butanolate, sec-butanolate, tert-butanolate, 2-methyl-2-butanolate, 2-methyl-2-pentanolate, 3-methyl-3-pentanolate, 3-ethyl-3-pentanolate, and further organic aliphatic, aromatic or heteroaromatic nitrogen bases, especially diazabicyclooctane, diazabicycloundecane and 4-dimethylaminopyridine and trialkylamine such as trimethyl- or triethyl-amine. The above-mentioned bases can also be used in admixture with one another.

Inorganic acids that come into consideration are, for example, hydrochloric acid, sulfuric acid or boron trifluoride.

Organic acids that are used are, for example, organic sulfonic acids or carboxylic acids such as unsubstituted or substituted aliphatic, cycloaliphatic, carbocyclic-aromatic, heterocyclic-aromatic or araliphatic sulfonic or carboxylic acids.

For example, it is possible to use, as aliphatic sulfonic acids, methane-, ethane-, n-propane- or hexane-sulfonic acid or corresponding fluoro-substituted derivatives thereof.

Aliphatic carboxylic acids are, for example, formic, acetic, propionic, butyric, pivalic, caproic, 2-ethylhexyl carboxylic acids or fatty acids such as lauryl acid, myricetin acid or stearic acid or fluoro-substituted derivatives thereof.

Examples of cycloaliphatic sulfonic or carboxylic acids are cyclohexanecarboxylic acids, camphor-10-sulfonic acid or fluoro-substituted derivatives thereof. Examples of carbocyclic-aromatic sulfonic acids are benzene-, toluene-, ethylbenzene-, isopropylbenzene-, dodecylbenzene- or dimethylbenzene-sulfonic acids, 2,4,6-triisopropylbenzene-sulfonic acid, 2,4,6-trimethylbenzene-sulfonic acid, naphthalene-sulfonic acid, -disulfonic acid or -trisulfonic acid and correspondingly alkyl- or fluoro-substituted derivatives thereof.

Examples of heterocyclic-aromatic sulfonic acids are pyridine-, thiophene- or pyrrole-sulfonic acids and correspondingly fluoro-substituted derivatives thereof.

Examples of carbocyclic-aromatic carboxylic acids are benzoic acid, toluene-, ethylbenzene-, isopropylbenzene- or dimethylbenzene-carboxylic acid, naphthalenecarboxylic acid or anthracenecarboxylic acid and correspondingly fluoro-substituted derivatives thereof. Examples of araliphatic carboxylic acids are benzylcarboxylic acids, α-methylbenzylcarboxylic acids and cinnamic acid and correspondingly fluoro-substituted derivatives thereof.

Furthermore, in a further embodiment of the process according to the invention, a C—H acid compounds is reacted with ketals in the presence of a base and then an acid. The function of the ketal is usually to protect the 3-carbonyl group temporarily against condensation during base-catalysed selective condensation at the 2-carbonyl group. After the condensation, the ketal is generally removed using acid and the carbonyl group liberated.

The compounds according to the invention are generally worked up and isolated using methods that are generally known to the person skilled in the art. The crude precipitated product is usually filtered off and the filter residue is washed with, preferably, a solvent in which the reaction product has only poor solubility. If desired, the crude product can also be subjected to purification operations before isolation. For that purpose, it is possible, for example, for the reaction-product-containing organic phase to be washed with water, especially with water containing hydrochloric acid or with a sodium hydroxide solution, and then to isolate the organic phase and to concentrate, preferably to dryness. In a further variant of working up, it is also possible for the organic reaction product to be concentrated directly by means of evaporation and then to be purified, for example by recrystallisation or separation by column chromatography. In the case of recrystallisation, isolation is usually carried out by means of filtration and subsequent washing of the filter residue with, preferably, a solvent in which the reaction product has only poor solubility. The reaction-product-containing organic phase, having been chromatographed on a column, can be concentrated directly by means of evaporation. If desired, the reaction products can be dried after isolation. For that purpose, there are usually used generally known drying apparatuses such as drying cabinets or paddle dryers.

For the preparation of compounds of formulae (IIa) or (IIb) it has proved especially advantageous to work in the presence of acids or anhydrides such as acetic acid or acetic anhydride.

The starting materials for this process are prepared analogously to known processes. Isatin compounds can be prepared by generally known methods, for example as described by W. C. Sumpter in Chem. Rev. 34, 413, 1944. The N-alkylation of isatins is also generally known and described, for example, by O. M. Radul et al. in Khimiya Geterotsiklicheskikh Soedinenii 353, 1983.

The preparation of oxobenzofuranyl compounds is likewise generally known or can be carried out analogously to known methods for the preparation of furanone unsubstituted in the 3-position and of 3-oxo-furanone compounds. Furanones unsubstituted in the 3-position can be prepared, for example, analogously to the process of H.-D. Becker, K. Gustafsson, J. Org. Chem. 42, 2966 (1977), from phenols by reaction with glyoxal.

Bisbenzofuranones are known and are prepared, for example, according to J. H. Wood, L. Cox, Org. Synth. III, 286 (1955); or (4,8-dimethyl-3,7-dihydro-benzo(1,2-b-4,5-b')difuran-2,6-dione is prepared, for example, according to L. I. Smith, J. Nichols, J. Am. Chem. Soc., 65,1739 (1943).

3-Oxo-furanone compounds can be prepared by oxidation of furanone compounds unsubstituted in the 3-position or by oxidation of 3-hydroxy-furanone compounds according to generally known methods for the oxidation of hydroxy compounds to keto compounds. Such methods are described, for example, in Houben-Weyl, Methoden der Organischen Chemie, 4th edition, Volume 4/1a & 4/1b. In J. Org. Chem., 56, page 6110 (1991), by Z-Ma, J. M. Bobbitt, oxidation using nitroxides is described. 3-Hydroxy-furanone compounds can be prepared analogously to the process for 3-hydroxy-benzofuranones described in U.S. Pat. No. 5,614, 572. 3-Oxo-furanone compounds can, moreover, be prepared analogously to the process of D. J. Zwaneburg and W. A. P. Reyen described in Synthesis, 624, of 1976.

A further embodiment relates to the preparation of bis (oxobenzofuranylidene-dihydroindolones) according to the invention from bis(furanone compounds) of formula (XXXVIII)

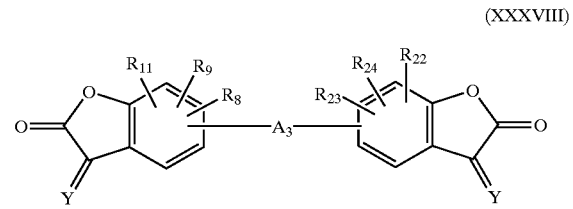

(XXXVIII)

or formula (XXXIX)

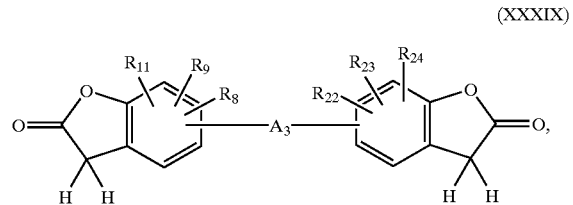

(XXXIX)

or from corresponding bis-isatin or -indoxyl compounds or mixtures thereof.

Analogous to the preparation of the bis compounds, it is possible to prepare the tris compounds or poly-compounds of tris- or poly-(oxobenzofuranylidene-dihydroindolones) from tris- or poly-(furanone compounds) or tris- or poly-(isatin or indoxyl) compounds, respectively. The preparation of polyisatins is known from GB-A 1 251 082.

It is also possible, of course, for many oxobenzofuranylidene-dihydroindolones to be prepared from other oxobenzofuranylidene-dihydroindolones, by chemically modifying the substituents of the latter which are in the form of functional groups without changing the basic oxobenzofuranylidene-dihydroindolone structure. The person skilled in the art will be acquainted with innumerable methods whereby substituents can be converted to other substituents, for example those disclosed in the series "Compendium of Organic Synthetic Methods" (Wiley & Sons, New York, 1971 onwards). Advantageous reaction conditions are those under which, taking into account the known reactivity of oxobenzofuranylidene-dihydroindolone, it is unlikely that its lactone or lactam bonds will be cleaved or its double bond will be reduced or otherwise modified. For example, new ester or amide derivatives can be prepared by generally known methods of synthesis such as described, for example, in Organic Syntheses, Collective Vol. I-VII. Special preference is given to esters that are prepared by transesterification or esterification of compounds of formula (Ia), (Ib), (IIa) or (IIb), for example using various alcohols, under generally known conditions of synthesis and catalysis, for example at temperatures of from 0° C. to 200° C., using amounts of alcohol of from 2 to 200 equivalents relative to one equivalent of the compound of formulae (Ia), (Ib), (IIa) or (IIb), optionally in the presence of a solvent.

Compounds of formulae (Ia), (Ib), (IIa) or (IIb) are advantageously used in an amount of from 0.01 to 70% by weight, usually from 0.01 to 30% by weight, preferably from 0.01 to 10% by weight, based on the organic or inorganic, high molecular weight or low molecular weight material, especially the high molecular weight organic material, to be coloured.

The invention relates also to a composition comprising an organic or inorganic, high molecular weight or low molecular weight material, especially a high molecular weight organic material, and at least one compound according to the invention or the above-described compositions according to the invention in a tinctorially effective amount, generally in the range from 0.01 to 70% by weight, especially from 0.01 to 30% by weight, preferably from 0.01 to 10% by weight, based on the organic or inorganic material.

The present invention relates also to the use of compounds or compositions according to the invention as colourants, especially for colouring or pigmenting organic or inorganic, high molecular weight or low molecular weight material, especially high molecular weight organic material.

It is, however, also possible to use the compounds and compositions according to the invention as mixtures, solid solutions or mixed crystals.

The compounds according to the invention may also be combined with colourants of a different chemical class, e.g. with dyes or pigments, for example selected from the group of diketopyrrolopyrroles, quinacridones, perylenes, dioxazines, anthraquinones, indanthrones, flavanthrones, indigos, thioindigos, quinophthalones, isoindolinones, isoindolines, phthalocyanines, metal complexes, azo pigments and azo dyes.

Depending on the nature of their substituents and the polymer to be coloured, the compounds according to the invention may be used as polymer-soluble dyes or as pigments. In the latter case it is advantageous for the products obtained on synthesis to be converted into a finely dispersed form, which can be carried out in a manner known per se. Depending on the compound and the intended use, it has proved advantageous to use the colourants as toners or in the form of preparations.

The high molecular weight material may be organic or inorganic and may refer to synthetic and/or natural substances. It may consist of, for example, natural resins or drying oils, natural rubber or casein or modified natural substances, such as chlorinated rubber, oil-modified alkyd resins, viscose, or cellulose ethers or esters, such as ethylcellulose, cellulose acetate, propionate or butyrate, cellulose acetobutyrate and also nitrocellulose, but especially completely synthetic organic polymers (thermosetting plastics and thermo-plastics), as can be obtained by polymerisation, for example by polycondensation or polyaddition. The class of the polymers includes, for example, polyolefins, such as polyethylene, polypropylene, polyisobutylene, also substituted polyolefins, such as polymerisation products of monomers such as vinyl chloride, vinyl acetate, styrene, acrylonitrile, acrylic acid esters, methacrylic acid esters, fluorinated polymerisation products, such as polyfluoroethylene or polytrifluorochloroethylene or a tetrafluoroethylene/hexafluoropropylene mixed polymerisation product, and also copolymerisation products of the said monomers, especially ABS (acrylonitrile/butadiene/styrene) or EVA (ethylene/vinyl acetate). From the series of the polyaddition and polycondensation resins there may be used, for example, condensation products of formaldehyde with phenols, so-called phenoplasts, and condensation products of formaldehyde and urea or thiourea, and also melamine, so-called aminoplasts, also the polyesters used as surface-coating resins, either saturated, such as alkyd resins, or unsaturated, such as maleic resins; also linear polyesters, polyamides, polyurethanes, polycarbonates, polyphenylene oxides, silicones or silicone resins.

The said high molecular weight compounds may be present on their own or in mixtures as plastic masses, melts or in the form of spinning solutions. They may also be present in the form of their monomers or in the polymerised state in dissolved form as film-formers or binders for surface-coatings or printing inks, such as boiled linseed oil, nitrocellulose, alkyd resins, melamine resins and urea-formaldehyde resins or acrylic resins.

The present invention relates furthermore to the use of the compounds or compositions according to the invention in the production of inks, for printing inks in printing processes, for flexographic printing, screen printing, the printing of packaging, security colour printing, intaglio printing or offset printing, for preliminary stages of printing and for printing textiles, for office or home use or for graphics applications, for example for paper goods, for ballpoint pens, felt-tip pens, fibre-tip pens, cardboard, wood, (wood)stains, metal, stamp pads or inks for impact-printing processes (using impact printing ink ribbons); in the production of colourants for surface-coatings that can be used in industry or commerce, for textile decoration and industrial labelling; especially colourants for roller coatings or powder coatings or for automotive lacquers, for high-solids (low-solvent), aqueous or metallic surface-coatings or for pigmented formulations for aqueous paints, for mineral oils, lubricating greases or waxes; in the production of coloured plastics for coatings, fibres, plates or for shaped substrates; in the production of non-impact-printing material for digital printing, for thermal wax transfer printing, ink-jet printing or for thermal transfer printing; in the production of colour filters, especially for visible light in the range from 400 to 700 nm, for liquid crystal displays (LCD) or charge combined devices (CCD); in the production of cosmetics, or in the production of
polymeric coloured particles, toners, dry copy toners, liquid copy toners or electrophotographic toners.

The present invention relates furthermore to inks comprising high molecular weight organic material and a tinctorially effective amount of a compound or composition according to the invention.

Processes for the production of inks, especially for ink-jet printing, are generally known and are described, for example, in U.S. Pat. No. 5,106,417.

The inks can be produced, for example, by blending the compounds according to the invention with polymeric dispersants. Blending of the compounds according to the invention with the polymeric dispersant is preferably carried out according to generally known methods of blending, such as stirring or mixing, the use of an intensive mixer or high-performance mixer (e.g. Ultraturrax®) being especially recommended.

When blending the compounds or compositions according to the invention with polymeric dispersants, an organic solvent that can be diluted with water is advantageously used.

The ratio by weight of the compounds or compositions according to the invention relative to the ink is advantageously selected in the range from 0.0001 to 75% by weight, preferably from 0.001 to 50% by weight, based on the total weight of the ink.

The present invention relates also to a process for the production of inks which comprises blending with one another high molecular weight organic material and a tinctorially effective amount of the compounds or compositions according to the invention.

The present invention relates also to colourants comprising high molecular weight organic material and a compound or composition according to the invention in a tinctorially effective amount.

The present invention relates in addition to a process for the production of colourants which comprises blending a high molecular weight organic material and a tinctorially effective amount of a compound or composition according to the invention.

The present invention relates furthermore to coloured plastics or polymeric coloured particles comprising a high molecular weight organic material and a compound or composition according to the invention in a tinctorially effective amount.

The present invention relates in addition to a process for the production of coloured plastics or polymeric coloured particles, which comprises blending with one another a high molecular weight organic material and a tinctorially effective amount of a compound or composition according to the invention.

The high molecular weight organic substances are coloured with the colourants or compositions in accordance with the invention, for example by admixing such a colourant, where appropriate in the form of masterbatches, with the substrates using roll mills or mixing or grinding apparatuses, as a result of which the colourant is dissolved or finely dispersed in the high molecular weight material. The high molecular weight organic material together with the admixed colourant is then generally processed using methods known per se such as calendering, compression moulding, extrusion, coating, spinning, pouring or injection moulding, as a result of which the coloured material usually obtains its final form. Admixture of the colourant can also be effected immediately prior to the actual processing step, for example by continuously and simultaneously feeding a colourant according to the invention in powder form and a granulated high molecular weight organic material and, optionally, also additional ingredients, such as additives, directly into the intake zone of an extruder wherein mixing occurs just before processing. Generally, however, it is preferable to mix the colourant into the high molecular weight organic material beforehand, since more uniform results can be achieved.

In order to produce non-rigid formed articles or to reduce their brittleness, it is frequently desirable to add so-called plasticisers to the high molecular weight compounds prior to forming. There may be used as plasticisers, for example, esters of phosphoric acid, phthalic acid or sebacic acid. In the process according to the invention, the plasticisers can be incorporated into the polymers before or after incorporation of the colourant. It is also possible, in order to achieve different colour shades, to add to the high molecular weight organic substances, in addition to the compounds or compositions according to the invention, constituents such as white, coloured or black pigments, in amounts desired in the particular case.

For the purpose of colouring surface-coatings and printing inks, the high molecular weight organic materials and the compounds or compositions according to the invention, optionally together with additional ingredients, such as fillers, dyes, pigments, siccatives or plasticisers, are finely dispersed or dissolved together in an organic solvent or solvent mixture, it being possible to use a procedure in which the individual components are dispersed or dissolved separately or in which a plurality thereof are dispersed or dissolved together, and only then all of the components combined. Processing is carried out using customary methods, for example by spraying, film-spreading or by one of the many printing methods, after which the surface-coating or the printing ink, where appropriate after drying beforehand, is advantageously cured thermally or by irradiation.

When the high molecular weight material to be coloured is a surface-coating, it may be a usual surface-coating or a specialist surface-coating, for example an automotive lacquer, especially a metal effect finish containing, for example, metal or mica particles.

Preference is given to the colouring of thermoplastic plastics, especially in the form of fibres, as well as printing inks. Preferred high molecular weight organic materials that can be coloured in accordance with the invention are very generally polymers having a dielectric constant $\geq 2.5$, especially polyesters, polycarbonate (PC), polystyrene (PS), polymethyl methacrylate (PMMA), polyamide, polyethylene, polypropylene, styrene/acrylonitrile (SAN) or acrylonitrile/butadiene/styrene (ABS). Especially preferred are polyesters, polycarbonate, polystyrene and PMMA. More especially preferred are polyesters, polycarbonate or PMMA, especially aromatic polyesters, which can be obtained by polycondensation of terephthalic acid, for example polyethylene terephthalate (PET) or polybutylene terephthalate (PBTP).

Special preference is given also to the colouring of mineral oils, lubricating greases and waxes using the compounds according to the invention.

The present invention relates furthermore to non-impact-printing material that comprises high molecular weight organic material and a compound or composition according to the invention in a tinctorially effective amount.

The present invention relates in addition to a process for the production of non-impact-printing material which comprises blending with one another a high molecular weight organic material and a tinctorially effective amount of a compound or composition according to the invention.

The present invention relates also to a process for the production of colour filters comprising a transparent substrate and, applied thereto, a red, a blue and a green layer in any order, which process comprises using an appropriately coloured compound or composition according to the invention in the production of each of the red, blue and green layers.

The designs of the differently coloured layers are preferably such that they do not overlap over at least 5% of their respective surface area and very especially do not overlap at all.

The colour filters can be coated, for example, using inks, especially printing inks, comprising the compounds or compositions according to the invention or can be prepared, for example, by blending a compound or composition according to the invention with chemically, thermally or photolytically structurable high molecular weight material ("resist"). Production can be continued, for example, analogously to the method described in EP-A 654 711, by application to a substrate, such as an LCD, followed by photo-structuring and developing.

The invention also encompasses a transparent substrate coated with a red, a blue and a green layer each having an appropriately coloured compound or composition according to the invention, the composition comprising pigmented high molecular weight organic material. The order of coating is generally immaterial. The designs of the differently coloured layers are preferably such that they do not overlap over at least 5% of their respective surface area and very especially do not overlap at all.

The present invention also relates, moreover, to colour filters comprising a transparent substrate and, applied thereto, a red, a blue and a green layer, each being obtainable from an appropriately coloured compound or composition according to the invention.

The present invention relates also to toners that comprise high molecular weight organic material and a or composition according to the invention in a tinctorially effective amount.

The present invention relates furthermore to processes for the production of toners which comprise blending with one another a high molecular weight organic material and a tinctorially effective amount of a compound or composition according to the invention or prepared in accordance with the invention.

In a particular embodiment of the process according to the invention, toners, surface-coatings, inks or coloured plastics are produced by processing masterbatches of toners, surface-coatings, inks or coloured plastics in roll mills or mixing or grinding apparatuses. In the present invention, "a tinctorially effective amount" of a compound or composition according to the invention or prepared in accordance with the invention generally denotes an amount of from 0.0001 to 99.99% by weight, especially from 0.001 to 50% by weight and more especially from 0.01 to 50% by weight, based on the total weight of the material pigmented or coloured therewith.

When the compounds or compositions according to the invention or prepared in accordance with the invention are present in the dissolved state in the polymers used, they are distinguished by a pure colour shade, high colour strength, high fastness to light and to weathering and fastness to heat, especially in PET, PMMA, PS and PC, and also by high fluorescence. The colourations obtained, for example in thermoplastics or thermosetting plastics, fibres, surface-coatings or printing inks, are distinguished by a pure colour shade, high colour strength, high saturation, high transparency, good fastness to overspraying, fastness to migration, fastness to rubbing, fastness to light, fastness to weathering and, especially, fastness to heat and also by a good gloss. The colourants possess good dispersibility and, generally, good solubilities in organic solvents. They are suitable for solar energy collectors and for the production of laser beams. Wonderful colour shades are obtained in mixtures comprising the compounds according to the invention. Especially advantageously, asymmetric oxobenzofuranylidene-dihydroindolones and also bis- or tris-(oxobenzofuranylidene-dihydroindolones) enable further colour shades to be obtained and offer the possibility, by means of selection of the substituents, of influencing their solubility.

EXAMPLES

Example 1

3-(5,7-Di-ert-butyl-2-oxo-benzofuran-3-ylidene)-1,
3-dihydro-indol-2-one 14.7 g (0.1 mol) of isatin, 24.6 g (0.1 mol) of 5,7-di-tert-butyl-3H-benzofuran-2-one, prepared analogously to the method of H.-D. Becker and K. Gustaffson described in J. Org. Chem., 42, 2966 of 1977, and 0.75 g of p-toluenesulfonic acid in 75 ml of acetic acid are heated at reflux under nitrogen for 17 hours. The reaction mixture is cooled to room temperature, the precipitate is filtered off and the filter residue is washed with methanol and then dried at 60° C. The yield is 27.7 g (74% of theory). Melting point: 277–284° C.

C: calculated/found 76.77/76.75; H: calculated/found 6.71/6.74; N: calculated/found 3.7313.56

Example 2

3-[7-tert-Butyl-2-oxo-3-(2-oxo-1,2-dihydro-indol-3-
ylidene)-2,3-dihydro-benzofuran-5-yl]-propionic
acid A) 3-(7-tert-Butyl-2-oxo-2,3-dihydro-benzofuran-5-yl)-propionic acid 66.7 g (0.3 mol) of 3-(3-tert-butyl-4-hydroxy-phenyl)-propionic acid (prepared analogously to the method described in JP-A2-63/227542) in 58 g (0.4 mol) of aqueous glyoxal solution (40% by weight) and 3 ml of hydrochloric acid (32% by weight) are heated at reflux in 200 ml of acetic acid for 6 hours. The mixture is then poured into 600 ml of ice-water and the precipitate is filtered off. The filter residue is washed with water and then dried at 60° C. g. Recrystallisation from toluene results in 54.3 g (69% of theory) of 3-(7-tert-butyl-2-oxo-2,3-dihydro-benzofuran-5-yl)-propionic acid. Melting point 167–169° C.

B) 7.36 g (0.05 mol) of isatin, 13.1 g (0.05 mol) of 3-(7-tert-butyl-2-oxo-2,3-dihydro-benzofuran-5-yl)-propionic acid from Example 2A and 0.5 g of p-toluenesulfonic acid are heated at reflux in 50 ml of acetic acid under nitrogen for 23 hours. The reaction mixture is cooled to room temperature, the precipitated solid is filtered off and the filter residue is washed with water and dried at 60° C. The yield is 12.2 g (63% of theory). Melting point 228–252° C.

C: calculated/found 70.58/70.31; H: calculated/found 5.41/5.52; N: calculated/found 3.58/3.40

Example 3

3-(5,7-Di-tert-butyl-2-oxo-benzofuran-3-ylidene)-1-
methyl-1,3-dihydro-indol-2-one 8.05 g (0.05 mol) of N-methylisatin (from Aldrich), 12.3 g (0.05 mol) of 5,7-di-tert-butyl-3H-benzofuran-2-one and 0.4 g of p-toluenesulfonic acid are heated at reflux in 40 ml of acetic acid under nitrogen for 19 hours. The suspension is cooled to room temperature, the precipitated solid is filtered off and the filter residue is washed with methanol and then dried at 60° C. The yield is 15.3 g (79% of theory). Melting point: 235–237° C.

C: calculated/found 77.09177.06; H: calculated/found 6.99/7.07; N: calculated/found 3.60/3.88

Example 4

3-[7-tert-Butyl-3-(1-methyl-2-oxo-1,2-dihydro-indol-3-ylidene)-2-oxo-2,3-dihydrobenzofuran-5-yl]-propionic acid 16.1 g (0.1 mol) of N-methylisatin, 26.2 g (0.1 mol) of 3-(7-tert-butyl-2-oxo-2,3-dihydrobenzofuran-5-yl)-propionic acid (see Example 2) and 2 g of p-toluenesulfonic acid are heated at reflux in 80 ml of acetic acid under nitrogen for 24 hours. The suspension is cooled to room temperature, diluted with 80 ml of methyl tert-butyl ether and then filtered. The filter residue is washed with methyl tert-butyl ether and then dried at 60° C. The yield is 28.5 g (70% of theory). Melting point: 231–232° C.

C: calculated/found 71.10/71.03; H: calculated/found 5.72/5.62; N: calculated/found 3.45/3.62

Example 5

3-(7-tert-Butyl-5-methoxy-2-oxo-benzofuran-3-ylidene)-1,3-dihydro-indol-2-one (Z/E mixture)

6.6 g (0.03 mol) of 7-tert-butyl-5-methoxy-3H-benzofuran-2-one (prepared analogously to the method from J. Org. Chem., 42 (1977) 2966) (colourless crystals having a melting point of 116–118° C. are obtained), 4.4 g (0.03 mol) of isatin and 0.25 g of p-toluenesulfonic acid are heated at reflux in 25 ml of acetic acid under nitrogen for 15 hours. 50 ml of ethanol are then added and the suspension is cooled to room temperature and filtered. The filter residue is washed with methanol and then dried at 60° C. The yield is 4.9 g (47% of theory). Melting point: 247–258° C.: calculated/found 72.19/72.09; H: calculated/found 5.48/5.52;

N: calculated/found 4.01/4.09

Example 6

3-(7-tert-Butyl-5-methoxy-2-oxo-benzofuran-3-ylidene)-1-methyl-1,3-dihydro-indol-2-one 11.0 g (0.05 mol) of 7-tert-butyl-5-methoxy-3H-benzofuran-2-one and 8.1 g (0.05 mol) of N-methylisatin and 1 g of p-toluenesulfonic acid are boiled in 40 ml of acetic acid under nitrogen for 24 hours. 40 ml of methanol are then added and the suspension is cooled to room temperature and filtered. The filter residue is washed with methanol; 100 ml of n-butanol are then added and heating at reflux is carried out for 15 minutes, followed by cooling to 5° C. and filtering. The filter residue is then dried at 60° C. 13.4 g (74% of theory) are obtained. Melting point: 188–190° C.

C: calculated/found 72.71/72.52; H: calculated/found 5.82/5.69; N: calculated/found 3.85/3.65

Example 7

[3-(7-tert-Butyl-5-methoxy-2-oxo-benzofuran-3-ylidene)-2-oxo-2,3-dihydro-indol-1-yl]-acetic acid A) (2,3-Dioxo-2,3-dihydro-indol-1-yl)-acetic acid tert-butyl ester 44.1 g (0.3 mol) of isatin, 62.5 g (0.45 mol) of potassium carbonate and 66.2 g (0.34 mol) of bromoacetic acid tert-butyl ester (from Aldrich) are stirred in 100 ml of N,N'-dimethylformamide at room temperature for 24 hours. The mixture is then poured into 800 ml of water, and the precipitate formed is filtered off, washed with water and dried at 60° C. After recrystallising once from toluene-hexane (1:1), 608 g (78% of theory) of product having a melting point of 119–121° C. are obtained.

B) 25.4 g (0.097 mol) of the (2,3-dioxo-2,3-dihydro-indol-1-yl)-acetic acid tert-butyl ester obtained above and 1 g of p-toluenesulfonic acid are boiled in 50 ml of acetic acid under nitrogen for 16 hours. 50 ml of water are then added and the suspension obtained is subsequently cooled to room temperature. The solid is filtered off, and the filter residue is washed with acetic acid (50% by weight) and dried at 60° C. The yield is 31.8 g (80% of theory). Melting point: 264–266° C.;

C: calculated/found 67.81/67.79; H: calculated/found 5.20/4.94; N: calculated/found 3.44/3.32

Example 8

5,7-Dibromo-3-(5,7-di-tert-butyl-2-oxo-benzofuran-3-ylidene)-1,3-dihydro-indol-2-one (Z/E mixture)

7.6 g (0.025 mol) of 5,7-dibromoisatin (prepared analogously to the method described in Collect. Czech. Chem. Commun., 55 (1990) 2963), 5.5 g (0.025 mol) of 7-tert-butyl-5-methoxy-3H-benzofuran-2-one and 0.25 g of p-toluenesulfonic acid are boiled in 25 ml of acetic acid under nitrogen for 17 hours. 40 ml of methanol are then added and the suspension obtained is cooled to 5° C. The precipitated solid is filtered off and the filter residue is washed with methanol and dried at 60° C. The yield is 11.9 g (94% of theory). Melting point: 232–256° C.

C: calculated/found 54.06/54.35; H: calculated/found 4.35/4.22; N: calculated/found 2.63/2.57

Example 9

5,7-Dibromo-3-(7-tert-butyl-5-methoxy-2-oxo-benzofuran-3-ylidene)-1,3-dihydro-indol-2-one (Z/E mixture)

7.6 g (0.025 mol) of 5,7-dibromoisatin, 6.15 g (0.025 mol) of 5,7-di-tert-butyl-3H-benzofuran-2-one and 0.5 g of p-toluenesulfonic acid are boiled in 25 ml of acetic acid under nitrogen for 21 hours. 40 ml of methanol are then added and the suspension obtained is cooled to 5° C. The solid then obtained is filtered off and the filter residue is washed with methanol and dried at 60° C. The yield is 10.7 g (80% of theory). Melting point: 303–314° C. C: calculated/found 49.73/49.46; H: calculated/found 3.38/3.45; N: calculated/found 2.76/2.73

Example 10

2-(5,7-Di-tert-butyl-2-oxo-benzofuran-3-ylidene)-1,2-dihydro-indol-3-one 20 g (0.08 mol) of 5,7-di-tert-butyl-3H-benzofuran-2-one, 13.2 g (0.08 mol) of 2-chloro-indol-3-one (prepared analogously to the method described in Synthesis, 496 (1974)) in 150 ml of toluene and 30 ml of triethylamine are stirred at 40° C. for 4 hours. 500 ml of ethyl acetate are then added and the mixture obtained is washed with 500 ml of dilute hydrochloric acid (5% by weight) and then with 500 ml of water. The ethyl acetate phase is separated off and then dried over sodium sulfate. The solid obtained is, after distilling off the solvent, recrystallised from butanol-toluene (1:1). The yield is 9.3 g (31% of theory).

Melting point: 290–292° C.

C: calculated/found 76.77/76.94; H: calculated/found 6.71/6.89; N: calculated/found 3.73/3.61

Example 11

2-(7-tert-Butyl-5-methoxy-2-oxo-benzofuran-3-ylidene)-1,2-dihydro-indol-3-one 23.5 g (0.160 mol) of isatin are introduced into 200 ml of chlorobenzene, and 35 g (0.168 mol) of phosphorus pentachloride are added. The suspension is heated slowly to 100° C. with vigorous formation of HCl and stirred at that temperature for 90 minutes. 100 ml of chlorobenzene and phosphorus oxychloride that forms are then distilled off. 35.2 g (0.160 mol) of 7-tert-butyl-5-methoxy-3H-benzofuran-2-one are added to the solution that remains behind, stirring is then continued at 130° C. for 2 hours and then concentration is carried out by distilling off 50 ml of chlorobenzene. 200 ml of methanol are then added and the suspension is subsequently cooled to 5° C. and then filtered. The filter residue is purified by chromatography on silica gel using a solvent mixture of toluene, ethyl acetate and methanol in the mixing ratio (4:3:3). The pure fractions are recrystallised once from butanol-toluene (1:1) and dried at 60° C. A yield of 6.7 g (12% of theory) is obtained. Melting point: 239–240° C.

C: calculated/found 72.19/72.03; H: calculated/found 5.48/5.42; N: calculated/found 4.01/4.17

Example 12a

Preparation of bisbenzofuranone 2,5-Dihydroxybenzene-1,4-diacetic acid, 10 g (44.2 mmol) (available from Aldrich), toluene, 500 ml, and acetic anhydride, 100 ml, are reacted at 90° C. for 4.5 hours. The reaction mixture is then cooled to 25° C. and filtered. The filter residue is washed with toluene, 50 ml, and then dried in a vacuum drying cabinet at 50° C. 7.1 g of bisbenzofuranone

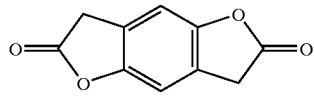

are obtained. The yield is 85% of theory.

Example 12b

Reaction of bisbenzofuranone with isatin

Bisbenzofuranone, 2.0 g (prepared according to Example 12a), isatin, 3.09 g (purum, available from Fluka) and toluenesulfonic acid, 0.5 g (purum, available from Fluka) are stirred in acetic acid, 30 ml, at 115° C. for 16 hours. The reaction mixture is filtered and the filter residue is washed with acetic acid, 30 ml, and methanol, 50 ml, and then dried in a vacuum drying cabinet at 80° C. 4.5 g of a violet powder of the compound of the following formula

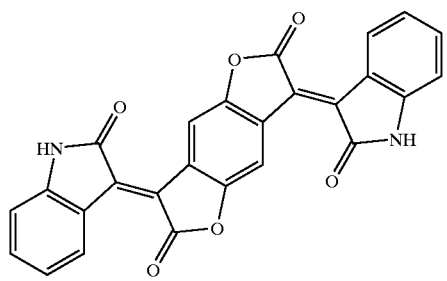

are obtained.

LDI-TOF(laser desorption ionisation/time of light): $(M^-)=448$

Example 13

Production of injection-moulded plates

General procedure: An oxobenzofuranylidene-dihydroindolone according to the invention is briefly mixed by hand with 1500 g of plastics that has been pre-dried at 473–543 K., and then mixed for 5 minutes at 50 rev./min. in a tumbling mixer. The mixture is then pre-extruded in a 25 mm single-screw extruder (Collin) at 543 K. The extrudate is then processed on a micro-processor-controlled injection-moulding machine (™Ferromatik FM 40, Klöckner) to form injection-mouldings (small plates measuring 65 mm×25 mm×1.5 mm). The dwell time of the polymer is, unless otherwise stated, 5 minutes, the dynamic pressure and the screw speed of rotation being kept low.

(a) 0.1 g of the oxobenzofuranylidene-dihydroindolone prepared in Example 1 is processed with polyethylene terephthalate ("PET") (™MELINAR PURA, ICI) into injection-mouldings in accordance with the general procedure, the articles being produced in the injection-moulding machine at (a1) 543 K, (a2) 553, (a3) 563 K and (a4) 573 K.

The example is repeated with the oxobenzofuranylidene-dihydroindolones of Examples 2 to 11.

The injection-mouldings are distinguished by excellent colour fastness properties, very high heat stability, high fastness to light, good resistance to migration and a high colour strength. (The colour fastness properties are determined visually against a standard or by means of colorimetry.)

(b) Example 13a is repeated except that a polybutylene terephthalate ("PBTB") (CRASTIN®S 600 from Ciba Specialty Chemicals) is used as the plastics. Furthermore, the injection-mouldings (various batches as a result of the selection of different temperatures) are in each case produced with a dwell time of 2 minutes at (b1) 533 K, (b2) 548 K and (b3) 563 K.

The example is repeated using the oxobenzofuranylidene-dihydroindolones of Examples 2 to 12.

The injection-mouldings are distinguished by excellent colour fastness properties, very high heat stability, high fastness to light, good resistance to migration and a high colour strength. (The colour fastness properties are determined visually against a standard or by means of colorimetry.)

What is claimed is:

1. An oxobenzofuranylidene-dihydroindolone of formula trans-(Ia) or cis-(Ib)

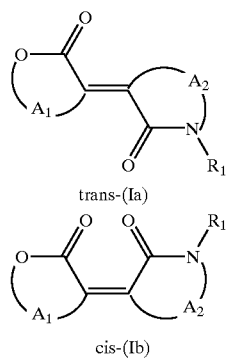

trans-(Ia)

cis-(Ib)

wherein $A_1$ and $A_2$ are each independently of the other unsubstituted or mono- to tetra-substituted 1,2-phenylene and $R_1$ is hydrogen, $C_1$–$C_{25}$alkyl, $C_5$–$C_{12}$cycloalkyl, $C_6$–$C_{24}$aryl, a heteroaromatic radical, —$(CH_2)_n$—$COR_2$ or —$(CH_2)_m$—$OR_3$, wherein $R_2$ is hydroxy, —OX, or, unsubstituted or mono- or poly-substituted by hydroxy, —OX or by amino, $C_1$–$C_{25}$alkoxy, $C_1$–$C_{25}$alkylamino or $C_1$–$C_{25}$dialkylamino, di($C_6$–$C_{24}$aryl)amino, $C_1$–$C_{12}$alkyl, $C_2$–$C_{24}$alkenyl, and X is a cation, and $R_3$ is hydrogen or —CO—($C_1$–$C_{25}$alkyl), and n and m denote each independently of the other a whole number in the range from 0 to 6, and a single C—C bond also may have been replaced by a corresponding ether unit, C—O—C, with the proviso that, when $R_1$ is hydrogen and $A_2$ is 1,2-phenylene, $A_1$ is not 4-chloro-3,5-dimethyl-1,2-phenylene or 3,5-dimethyl-1,2-phenylene.

2. An oxobenzofuranylidene-dihydroindolone according to claim 1, wherein $A_1$ is

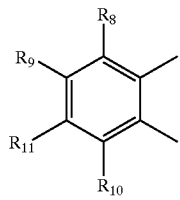

and $A_2$ is

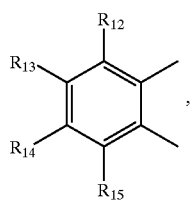

wherein $R_8$, $R_9$, $R_{11}$, $R_{10}$, $R_{12}$, $R_{13}$, $R_{14}$ and $R_{15}$ are each independently of the others hydrogen, halogen, cyano, —$NO_2$, —$R_{16}$, —$NR_{17}R_{18}$, —$NR_{19}COR_{17}$, —$NR_{19}COOR_{17}$, —$N=CR_{17}R_{18}$, —$CONR_{19}R_{20}$, —$OR_{17}$, —O—($C_1$–$C_{12}$alkylene)—COOX, —O—($C_1$–$C_{12}$alkylene)—COOH, —O—($C_1$–$C_{12}$alkylene)—O—CO—$R_{17}$, —O—($C_1$–$C_{12}$alkylene)—$COOR_{17}$,
—O—($C_1$–$C_{12}$alkylene)—$CONR_{19}R_{20}$, —O—($C_1$–$C_{12}$alkylene)—$OR_{17}$,
—($C_1$–$C_{12}$alkylene)—O—CO—$R_{17}$,
—($C_1$–$C_{12}$alkylene)—$OR_{17}$, —$COOR_{17}$,
—($C_1$–$C_{12}$alkylene)—$COOR_{17}$,
—($C_1$–$C_{12}$alkylene)—$CONR_{19}R_{20}$,
—($C_1$–$C_{12}$alkylene)—COOX,
—($C_1$–$C_{12}$alkylene)—COOH,
—COOX, —COOH, —$SR_{17}$, —$SOR_{17}$, —$SO_2R_{17}$, —$SO_2NR_{19}R_{20}$, —$SO_3R_{17}$, $SO_3H$ or $SO_3X$, wherein $R_{17}$, $R_{18}$, $R_{19}$ and $R_{20}$ are each independently of the others hydrogen or $R_{16}$, and $R_{16}$ is, unsubstituted or mono- or poly-substituted by halogen, hydroxy, amino, oxo, carboxy, cyano, —$COOR_{18}$ or by —COOX, $C_1$–$C_{25}$alkyl, $C_5$–$C_{12}$cycloalkyl or $C_2$–$C_{24}$alkenyl, which may be uninterrupted or interrupted one or more times by O, S or N—($C_1$–$C_{25}$alkyl), N—($C_2$–$C_{24}$alkenyl) when the alkyl has more than two and the alkenyl more than three carbon atoms, or is, unsubstituted or mono- or poly-substituted by halogen, nitro, cyano, —$OR_{18}$, —$SR_{18}$, —$NR_{19}R_{20}$, —$CONR_{19}R_{20}$, —$COOR_{18}$, —COOX, —COOH, —$SO_2R_{18}$, —$SO_2NR_{19}R_{20}$, —$SO_3R_{18}$, —$SO_3X$, —$SO_3H$, —$NR_{19}COR_{18}$ or by —$NR_{19}COOR_{18}$, $C_6$–$C_{18}$aryl, $C_7$–$C_{18}$aralkyl or heteroaryl or $R_{19}$ and $R_{20}$, together with the nitrogen atom linking them, are unsubstituted or mono- to tetra-$C_1$–$C_4$alkyl-substituted pyrrolidinyl, piperidyl, piperazinyl or morpholinyl, or are carbazolyl, phenoxazinyl or phenothiazinyl.

3. A composition comprising at least one oxobenzofuranylidene-dihydroindolone according to claim 1.

4. A process for the preparation of an oxobenzofuranylidene-dihydroindolone of formula trans-(Ia) or cis-(Ib) according to claim 1 by reaction of a benzofuranone compound with an isatin compound in the presence of an acidic or basic catalyst, which process comprises reacting a compound of formula (XXIX)

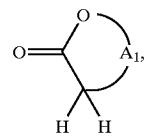

(XXIX)

wherein $A_1$ is unsubstituted or mono- to tetra-substituted 1,2-phenylene, with a compound of formula (XXX) or (XXXa)

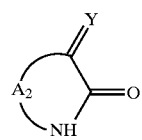

(XXX)

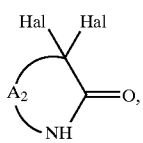

(XXXa)

wherein
Y is O, S, NH, N—($C_1$–$C_{24}$alkyl), N—($C_5$–$C_{18}$aryl) or N—($C_7$–$C_{28}$aralkyl) and
Hal is halogen, and
$A_2$ is unsubstituted or mono- to tetra-substituted 1,2-phenylene.

5. An oxobenzofuranylidene-dihydroindolone according to claim 1, wherein $A_1$ is

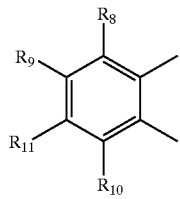

wherein
$R_8$, $R_9$, $R_{11}$, $R_{10}$, $R_{12}$, $R_{13}$, $R_{14}$ and $R_{15}$ are each independently of the others hydrogen, halogen, cyano, —$NO_2$, —$R_{16}$, —$NR_{17}R_{18}$, —$NR_{19}COR_{17}$, —$NR_{19}COOR_{17}$, —$N{=}CR_{17}R_{18}$, —$CONR_{19}R_{20}$, —$OR_{17}$, —O—($C_1$–$C_{12}$alkylene)—COOX, —O—($C_1$–$C_{12}$alkylene)—COOH, —O—($C_1$–$C_{12}$alkylene)—O—CO—$R_{17}$, —O—($C_1$–$C_{12}$alkylene)—COOR$_{17}$, —O—($C_1$–$C_{12}$alkylene)—CONR$_{19}$R$_{20}$, —O—($C_1$–$C_{12}$alkylene)—OR$_{17}$, —($C_1$–$C_{12}$alkylene)—O—CO—$R_{17}$, —($C_1$–$C_{12}$alkylene)—OR$_{17}$, —COOR$_{17}$, —($C_1$–$C_{12}$alkylene)—COOR$_{17}$, —($C_1$–$C_{12}$alkylene)—CONR$_{19}$R$_{20}$, —($C_1$–$C_{12}$alkylene)—COOX, —($C_1$–$C_{12}$alkylene)—COOH, —COOX, —COOH, —SR$_{17}$, —SOR$_{17}$, —SO$_2$R$_{17}$, —SO$_2$NR$_{19}$R$_{20}$, —SO$_3$R$_{17}$, SO$_3$H or SO$_3$X, wherein
$R_{17}$, $R_{18}$, $R_{19}$ and $R_{20}$ are each independently of the others hydrogen or $R_{16}$, and $R_{16}$ is, unsubstituted or mono- or poly-substituted by halogen, hydroxy, amino, oxo, carboxy, cyano, —COOR$_{18}$ or by —COOX, $C_1$–$C_{25}$alkyl, $C_5$–$C_{12}$cycloalkyl or $C_2$–$C_{24}$alkenyl, which may be uninterrupted or interrupted one or more times by O, S or N—($C_1$–$C_{25}$alkyl), N—($C_2$–$C_{24}$alkenyl) when the alkyl has more than two and the alkenyl more than three carbon atoms, or is, unsubstituted or mono- or poly-substituted by halogen, nitro, cyano, —OR$_{18}$, —SR$_{18}$, —NR$_{19}$R$_{20}$, —CONR$_{19}$R$_{20}$, —COOR$_{18}$, —COOX, —COOH, —SO$_2$R$_{18}$, —SO$_2$NR$_{19}$R$_{20}$, —SO$_3$R$_{18}$, —SO$_3$X, —SO$_3$H, —NR$_{19}$COR$_{18}$ or by —NR$_{19}$COOR$_{18}$, $C_6$–$C_{18}$aryl, $C_7$–$C_{18}$aralkyl or heteroaryl, or $R_{19}$ and $R_{20}$, together with the nitrogen atom linking them, are unsubstituted or mono- to tetra-$C_1$–$C_4$alkyl-substituted pyrrolidinyl, piperidyl, piperazinyl or morpholinyl, or are carbazolyl, phenoxazinyl or phenothiazinyl.

* * * * *